US006645756B1

(12) United States Patent
Criddle et al.

(10) Patent No.: US 6,645,756 B1
(45) Date of Patent: Nov. 11, 2003

(54) METHOD FOR REMEDIATION OF AN ENVIRONMENT CONTAMINATED WITH CARBON TETRACHLORIDE

(75) Inventors: Craig Criddle, Okemos, MI (US); Michael Dybas, Lansing, MI (US); Greg Tatara, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 08/370,551

(22) Filed: Jan. 9, 1995

Related U.S. Application Data

(63) Continuation of application No. 08/062,072, filed on May 14, 1993, now abandoned.

(51) Int. Cl.[7] .................................................. B09B 3/00
(52) U.S. Cl. ..................... 435/262.5; 435/262; 435/874; 210/601
(58) Field of Search .............................. 435/262, 262.5, 435/874; 210/601

(56) References Cited

PUBLICATIONS

Lewis, Thomas A., et al., Applied and Environmental Microbiology, p. 1635–1641 (1993).
Merck Index 11th Ed., p. 330.
C. Criddle et al., 1990, App. and Environ. Microbiol., 56:3240–3246, "Transformation of Carbon Tetrachloride by Pseudomonas sp. Strain KC under Denitrification Conditions".
M. Sittig, Ed., Noyes Pub., NJ, 1985, Handbook of Toxic and Hazardous Chemicals and Carcinogens, 2nd Ed, pp. 140 and 168.
E. Nyer, 1985, in Groundwater Treatment Tech., Van Nostrand Reinhold, NY, pp. 35–83, "Treatment for Organic Contaminants: Physical/Chemical Methods".
R. Harvey, 1991, in Modeling the Envron. Fate of Microorganisms, C.J. Hurst, ed., ASM, Washington, DC, pp. 89–114, "Parameters Involved in Modeling Movement of Bacteria in Groundwater".
P. Kearney et al., 1988, in Biotechnology for Crop Protection, ACM Symp., 379:352–358, "Methods Used to Track Introduced Genetically Engineered Organisms".
N. Pace et al., 1985, Analyzing Natural Microbial Populations by rRNA Sequence, ASM News, 51:4–12.
S. Silver et al., 1990, Pseudomanas Biotransformations, Pathogenesis, and Evolving Biotechnology, ASM Publ., Washington DC, pp. 101–267, "Site–Directed Mutagenesis of the Pseudomonas cam Operon".

Primary Examiner—Curtis E. Sherrer
(74) Attorney, Agent, or Firm—Ian C. McLeod

(57) ABSTRACT

A method of remediating an environment contaminated with carbon tetrachloride by introducing Pseudomonas strain sp. KC (PsKC) into the environment under iron limiting conditions and converting the carbon tetrachloride directly to carbon dioxide and a non-volatile water soluble fraction. Further, conditions providing a niche advantage for PsKC in accordance with the invention allow for the use of PsKC as a vector in various other environmental conditions for introducing specific activities of the PsKC, whether naturally occurring or genetically altered, into those environments.

5 Claims, 4 Drawing Sheets

METHOD FOR REMEDIATION OF AN ENVIRONMENT CONTAMINATED WITH CARBON TETRACHLORIDE

CROSS-REFERENCE

This application is a continuation of application Ser. No. 08/062,072, filed May 14, 1993, now abandoned.

TECHNICAL FIELD

The present invention relates to the use of microorganisms for the remediation of environments, such as contaminated groundwater, soil and aquifer materials. Further, the present invention relates to bioaugmentation of microorganisms in situ. More specifically, the present invention relates to the bioaugmentation and other uses of Pseudomonas strain sp. KC.

BACKGROUND OF THE INVENTION

Microbes have been well-characterized with regard to their ability to dehalogenate various compounds in nature. It has been recognized that this activity can potentially be exploited for in situ bioremediation of contaminated groundwater and the like.

Carbon tetrachloride is presently abundant as a contaminant in groundwater and aquifers. Carbon tetrachloride has been proven to pose health and cancer risks (Sittig, Ed. Handbook of Toxic and Hazardous Chemicals and Carcinogens, 2d Ed., Noyes Pubs. N.Y. (1985)). In typical contaminated areas, chloroform is the major breakdown product of carbon tetrachloride. However, chloroform has also been associated with health and cancer risks (Sittig, M. Ed. Handbook of Toxic and Hazardous Chemicals and Carcinogens, 2d Ed., Noyes Pubs. N.Y. (1985)).

PsKC has been found capable of transforming carbontetrachloride. The major products of the transformation of carbon tetrachloride by PsKC were found to be carbon dioxide and a still unidentified water soluble fraction. Significantly, no chloroform was produced in the reaction.

Previous remediation methods utilize extraction of groundwater coupled with above-ground treatment by air stripping or adsorption to activated carbon (Nyer, E. K., Groundwater Treatment Technology, Van Nostrand Reinhold, N.Y. (1985)). Air stripping uses large volumes of air to flush and dilute carbon tetrachloride out of water and absorption binds carbon tetrachloride to a solid material. These methods essentially transfer carbon tetrachloride from one media to another without destroying it, thereby leaving the contaminant for disposal.

The present invention provides a remediation system which can breakdown carbon tetrachloride directly to carbon dioxide without the concomitant production of chloroform. Field scale expression of a microbial trait/activity which has been characterized in a pure culture, laboratory environment involves overcoming several complex problems. Factors such as competition with indigenous microbes, parasitism, nutrient availability and other chemical niche properties, combined with certain physical features of environments (Harvey, R. W., Parameters Involved in Modeling Movement of Bacteria in Ground Water, pp. 89–114. In C. J. Hurst (ed.), Modeling the Environmental Fate of Microorganisms, ASM. Washington, D.C. (1991)) influence the persistence and fate of added microbes. In addition, expression of the desired activity may be influenced by factors such as ionic strength, pH and trace metal levels which while easily controlled in the lab are difficult to manipulate on a field scale.

The present invention describes modifications that can be made to create a suitable niche for the growth of the PsKC in an environment.

Bioaugmentation is a potentially useful means for introducing desirable activities into an existing environmental population or ecosystem. By creating a favorable environment or niche for a specific microbe, activities can very often be introduced into an environment by utilizing the microbe as a vector. The activity can be a naturally occurring activity of the microbe or a genetically altered activity. In either case the new or additive activity is introduced into the environment to perform a desired function. For example enzymatic activities expressed by a microorganism in situ have a large number of potential uses, ranging from production of desirable compounds to remediation of unwanted waste compounds. Although the preferred embodiment of the present invention provides a remediant use of PsKC, the present invention further provides means which can be used for the expression of other naturally occurring enzymatic activities or activities occurring as a result of a genetic modification of the PsKC.

A niche is a term of art known to ecologists. In the present invention the environment is modified in a way that will often create a niche that enables one to introduce PsKC into an environment and have the strain persist in a way that would otherwise not be possible. The PsKC can then be used, as discussed above to provide a desired function which may alter the region, such as catalyzing the degradation of the environmental pollutant.

SUMMARY OF THE INVENTION

The present invention provides a method of remediating an environment of carbon tetrachloride contamination by introducing Pseudomonas sp. strain KC (PsKC) into the environment under iron limiting conditions and converting the carbon tetrachloride directly to carbon dioxide and a non-volatile water soluble fraction.

Additionally, the present invention provides a niche advantage for PsKC in an environment by adjusting the pH of the environment to about pH 7.8 to 9.2 prior to introducing the PsKC into the environment.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

Figure 1:
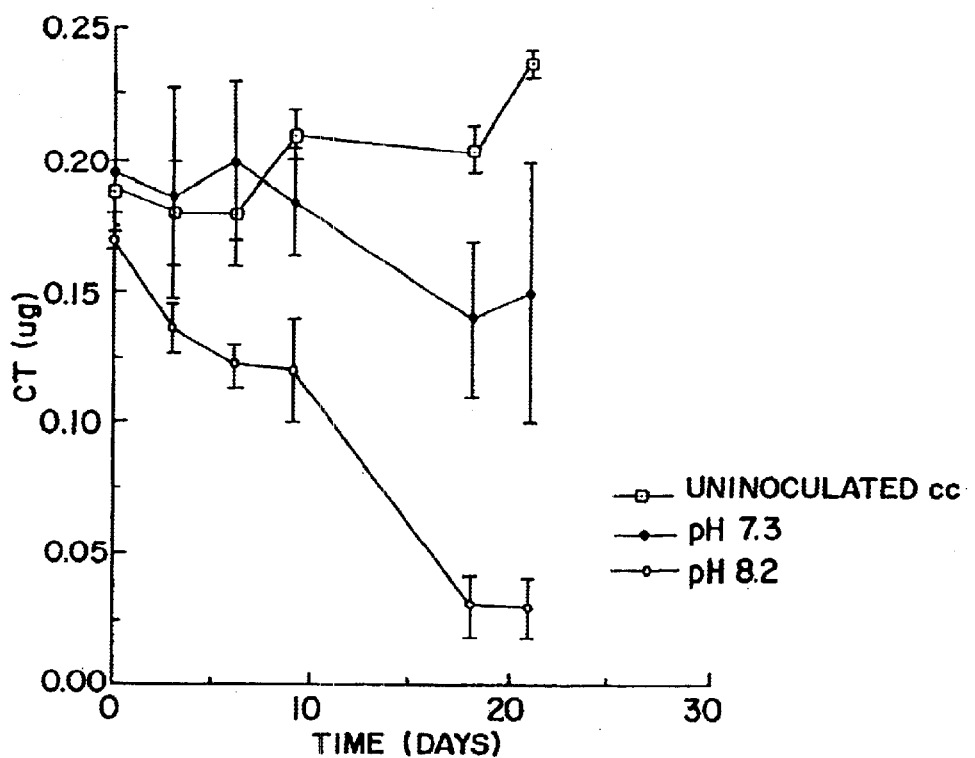
FIG. 1 is a graph showing pH dependence of CT transformation in soil. 286 g sandy Michigan soil (Metea type soil, B horizon, MSU campus) per liter tap water was prepared as a slurry and the pH was raised to 7.3 or 8.2 by addition of KOH. Samples (100 ml) were dispensed into 120 ml serum vials. Headspace was replaced with nitrogen. Pseudomonas KC (1% inoculum Nutrient Broth grown culture) was added as indicated. All values represent averages of three independent cultures, and the error bars indicate the standard deviations.

The present invention provides means for the use of Pseudomonas strain sp. KC (PsKC) for various purposes. More specifically, the present invention utilizes the capability of the PsKC to break down carbon tetrachloride in a contaminated environment in combination with a method of creating a niche for PsKC such that it can be used in an environment containing diverse microbial populations, such as aquifers, bioreactors, and the like.

PsKC is an aquifer-derived organism that transforms carbon tetrachloride to carbon dioxide and an unidentified non-volatile product without chloroform production under denitrifying conditions (Criddle, C. W., et al., App. and Environ. Microbiol. Vol, 56, No. 11, 3240–3246 (1990)). PsKC has been deposited in the DSM culture collection and is identified by Deposit Number 7136.

| | |
|---|---|
| Nitrate reductase | + |
| Phenylalanine | − |
| Citrate | + |
| Urea | − |
| Lysine | − |
| Arginine | − |
| Ornithine | − |
| Sucrose | − |
| Malonate | + |
| Anaerobic glucose | − |
| Adonitol | − |
| Aerobic glucose | + |
| Maltose | − |
| Arabinose | − |
| Inositol | − |
| Raffinose | − |
| Sorbitol | − |
| Lactose | − |
| Rhamnose | − |
| Growth with nitrite | + |
| Oxidase | + |
| Xylose | − |
| Glycerol | + |

One aspect of the present invention provides a method of remediating an environment, such as water, soil and the like, in situ as well as in bioreactors, of carbon tetrachloride contamination by the general steps of introducing the PsKC into the affected region of the environment and converting the carbon tetrachloride directly to carbon dioxide and a non-volatile water soluble fractions. Critical to the method is the ability of augmenting the environment in a manner that allows for the persistence of PsKC and allowing it to perform the remediation function in environments wherein the PsKC would not normally be competitive. This niche advantage is created by adjusting the pH of the affected region of the environment into which the PsKC is introduced to about 7.8 to 8.2 and then introducing the PsKC into the environment. As demonstrated in the experimental section below, the pH adjustment allows the naturally isolated PsKC microorganism to compete with soil microbial flora and express activities, such as the activity for breaking down the carbon tetrachloride to carbon dioxide, in the presence of indigenous soil microorganisms.

An advantage of the use of the present invention is that it can be used in a transitory manner. The pH of the environment can be adjusted temporarily thereby transiently creating a niche for PsKC. Once the pH adjustment is either reversed or simply not maintained, the niche ceases to exist. Hence, the PsKC can be preferentially grown in an environment for a purpose of solving an environmental problem and when the problem is solved, the niche can be removed.

Generally, the protocol includes the steps of initially adjusting the pH of an environment such as an aquifer or groundwater to the preferred pH range of 7.8 to 8.2. The culture of PsKC would be pumped or injected into the aquifer or groundwater source and supplemented with required growth factors including electron donors, such as acetate or glycerol; electron acceptors, such as nitrate and other nutrients if any are limiting at the site. These growth limiting factors can be supplied by various means including alternate pulsing of growth factors at a single well, addition of separate growth factors in separate wells with downstream mixing; or direct introduction of all required growth factors at a single well.

Finally, the dispersion of the bacteria and expression of the activity of the bacteria would be monitored by means well known in the art.

More specifically, the following protocol can be used.

Niche Adjustment

Prior to addition of PsKC, the pH of the materials as adjusted to pH 7.8–9.0 by addition of KOH or NaOH. Direct injection or pump controlled injection of aqueous base solution is combination with pH measurements of the material or ground water extracted from the materials is used to control and monitor pH. Nutrients are added by direct injection or pump controlled injection and are measured by laboratory practices standard in the arts (examples are acetate and phosphate measured by ion chromatographic analysis of extracted ground water samples).

Inoculation/Pseudomonas KC Addition

Cultures of Pseudomonas KC were grown under aerobic conditions or denitrifying conditions. Cells were added to a reasonable density by direct injection or pump controlled injection to samples containing carbon tetrachloride under denitrifying conditions.

Analytical

Carbon tetrachloride levels are followed by headspace gas chromatography.

Monitoring of Bacterial Movement

A enumeration/screening method based on colony morphology and siderophore production is used to follow the bacteria. Several methodologies known in the arts such as Biolog™ and probe technologies (Kearne, P. C., et al., Methods Used to Track Introduced Genetically Isolated Organisms. ACS Symp., 379:352–358 (1988); Pace, N. R., et al., Analyzing Natural Microbial Populations by rRNA sequence. ASM News, 51:4–12 (1985)) are being pursued to enhance detection and monitoring bacteria movement.

Another aspect of the present invention recognizes that the method of augmenting the growth of the PsKC in an environment, such as water and soil sources as well as aquifers, bioreactors, and the like, can be utilized to introduce the PsKC to bioaugment an environment with desirable activities outside the scope of remediation. That is, other activities, such as other enzymatic activities and non-enzymatic (e.g. siderophores, extracellular polysaccharides, cofactors, etc.) which may or may not be related to bioremediation can be expressed by genetically altered strains of PsKC for various potential uses, ranging from the production of desirable compounds to remediation of unwanted waste compounds in a manner which potentiates the method described above. Alternatively, the introduction of PsKC to environments that have been modified to provide a niche for PsKC can allow delivery of native activities of the PsKC to the environment. For example, unaltered PsKC can be used as a vector to provide activities such as toluene degradation and dichloromethane degradation, as well as other naturally occurring activities into an environment.

More specifically, this aspect of the present invention provides a method of augmenting growth of the PsKC in an environment by adjusting the pH of the environment or region of the environment to about 7.8 to 8.2 prior to introducing the PsKC into the environment. The PsKC may be a genetically modified strain having a specific activity introduced into the PsKC by genetic modification thereby bioaugmenting the source with a specific activity by introducing the genetically modified strain of the PsKC into the source. For example, the PsKC can have an increased activity of a specific enzyme. As the present invention provides means for allowing the PsKC to survive in the environment in competition with the indigenous microorganisms and other factors therein, the added desirable activity of the genetically modified PsKC can be expressed in the environment. In other words, the present invention allows the PsKC to act as a vector for delivering genetically engineered activities into an environment. As stated above, the PsKC can also introduce activities of nongenetically modified PsKC into the environment.

The PsKC can be modified by various means well known in the art (Silver, S., et al., Ed. Pseudomonas: Biotransformations, Pathogenesis and Evolving Biotechnology. ASM Publications, Washington, D.C. (1990)).

The present invention can be utilized as a delivery mechanism for an indigenous activity possessed by the present invention or as a vector for delivering the genetically engineered activities as discussed above. In practice, this can be accomplished by adjusting the pH of the aquifer, groundwater, soil, or other environment such as a bioreactor to the pH of 7.8 to 8.2. The PsKC can be pumped or injected as a culture into the environment, the PsKC having the desired genotype/phenotype. As discussed above, growth factors and nutrients can be supplemented into the environment if any are limiting at the site. Finally, the dispersion of the bacteria and expression of the activity are monitored.

The preferred method of enumerating and monitoring the persistence of PsKC obtained from the various sources discussed above while transforming carbon tetrachloride to carbon dioxide generally includes the steps of obtaining a sample from the source which need be monitored, inoculating the sample onto minimal media plates using acetate as a sole carbon source, and screening the unique morphology and iron binding activity of the PsKC on siderophore assay agar plates. The screening methods can be developed by those skilled in the art (Pace, N. R., et al., Analyzing Natural Microbial Populations by rRNA sequence. ASM News, 51:4–12 (1985)).

The above aspects of the present invention can be utilized in combination so as to provide means for remediating contaminated water and soil sources or other environments of carbon tetrachloride utilizing indigenous activities of the PsKC or genetically altered PsKC for either remediation purposes or other purposes.

EXPERIMENTAL SECTION

The following experimental section demonstrates the kinetics of carbon tetrachloride transformation by PsKC, and accelerated carbon tetrachloride transformation obtained in iron-rich groundwaters and soil slurries by adding the PsKC after the pH adjustment in accordance with the present invention to thereby augment the growth of the PsKC.

Chemicals

Carbon tetrachloride (CT, 99% purity) was obtained from Aldrich Chemical Co. Milwaukee, Wis. All chemicals for media preparation were ACS reagent grade (Aldrich or Sigma Chemical Co.), and all water used was 18 megohm resistance or greater.

Media Preparation and Growth Conditions

Medium D [3] container (per liter of deionized water) 2.0 g of $KH_2PO_4$, 3.5 g of $K_2HPO_4$, 1.0 g of $(NH_4)_2SO_4$, 0.5 g of $MgSO_4 \cdot 7H_2O$, 1 milliliter of trace nutrient stock TN2, 1 milliliter of 0.15 M $Ca(NO_3)_2$, 3.0 g of sodium acetate, and 2.0 g of sodium nitrate. Medium D was prepared with trace nutrient stock solution TN2. Stock solution TN2 container (per liter of deionized water) 1.36 g of $FeSO_4 \cdot 7H_2O$, 0.24 g of $Na_2MoO_4 \cdot 2H_2O$, 0.25 g of $CuSO_4 \cdot 5H_2O$, 0.58 g of $ZnSO_4 \cdot 7H_2O$, 0.29 g of $Co(NO_3)_2 \cdot 6H_2O$, 0.11 g of $NiSO_4 \cdot 6H_2O$, 35 mg of $Na_2SeO_3$, 62 mg of $H_3BO_3$, 0.12 g of $NH_4VO_3$, 1.01 g of $MnSO_4 \cdot H_2O$, and 1 ml of $H_2SO_4$ (concentrated). Some experiments used different trace metal preparations to study their effects on CT transformation. TN2-Cu and TN2-Fe stock solutions lacked $CuSO_4 \cdot 5H_2O$ and $FeSO_4 \cdot 7H_2O$, respectively, but were otherwise identical to TN2. After addition of all essential media components, medium D was adjusted to a desired initial pH of 8.0 or 8.2 with 3N KOH. This final adjustment in pH resulted in the formation of a white precipitate. The resulting medium was autoclaved at 121° C. for 30 minutes and transferred to an anaerobic glove box for degassing.

Precipitate-free medium D was prepared as follows: medium D (adjusted to an initial pH of 8.0 or 8.2) was autoclaved at 121° C. for 30 minutes, transferred to an anaerobic glove box for degassing and quiescent settling of precipitate, and decanted after 24 hours. The precipitate-free and oxygen-free decanted medium was re-autoclaved for 30 minutes at 121° C. and cooled before use. Precipitate-free medium D contained 24 mM acetate, 25 mM $PO_4^{3-}$, 19 mM $NO_{3-}$, and 3.8 nM iron, as determined by atomic absorption spectroscopy and ion chromatography.

Cultures were grown under a $N_2$ atmosphere in one of three different containers (Criddle, C. W., et al., App. and Environ. Microbiol. Vol. 56, No. 11, 3240–3246 (1990)) 28 mL serum tubes (Bellco Glass NO. 2048–00150), a modified one-liter Wheaton Bottle as described by Balch and Wolfe (Balch, W. E., R. S. Wolfe, J. Bacteriol. 137:264–273 (1979)), and (Nyer, E. K., Groundwater Treatment Technology, Van Nostrand Reinhold, N.Y. (1985)) 250 mL (8 oz.) bottles sealed with screw-cap Mininert valves (Alltech catalog number 95326). Both the serum tubes and the modified Wheaton bottles were sealed with Teflon®-faced butyl rubber septa (West Catalog number 1014–4852) and aluminum crimp seals. All cultures were shaken at 100–150 rpm at 20–23° C. Strain KC did not transform carbon tetrachloride at temperatures PsKC was also deposited under the Budapest Treaty with the American Type Culture Collection on Jun. 29, 1994 as ATCC 55595 above 25° C. and it did not grow at temperatures above 30° C. (data no shown). Culture manipulations were typically performed in a Coy anaerobic glove box (Coy Laboratories, Ann Arbor, Mich.) under an atmosphere of 98% $N_2$ and 2% $H_2$. Oxygen level was monitored continuously with a Coy gas detector model number 10. Hungate technique was used for anaerobic manipulations outside the glove box.

Analytical Methods

All bottles used to evaluate carbon tetrachloride transformation were sealed with pressure tested screw-cap Mininert valves or Teflon®-lined butyl rubber stoppers. Carbon tetrachloride was assayed by removing 0.1 mL of headspace gas with a 0.25 or 0.5 mL Precision gas-tight syringe (Alltech catalog number 050032), closing the syringe valve, inserting the syringe needle through the injection port septum, opening the syringe valve, and injecting the sample into the GC. For ppb concentrations, the GC e-was a Perkin Elmer model 8500 equipped with a 100/120 mesh column (10% Alltech CS-10 on a Chromsorb W-AW, Alltech catalog number 12009 PC) and an electron capture detector with nitrogen carrier (40 mL/min) and nitrogen make-up (27 mL/min). For ppm concentrations, the GC was a Hewlett Packard 5890 gas chromatograph operated isothermally at 150° C. and equipped with a DG 624 column (J&W Scientific catalog number 125–1334) and a flame ionization detector (hydrogen flowrate=100 mL/min, air flowrate=250 mL/min). The carrier gas was nitrogen (16 mL/min).

External standard calibration curves were prepared by addition of a primary standard (7.8 ng carbon tetrachloride pr $\mu$g carbon tetrachloride per $\mu$L methanol) to secondary standard water solutions having the same gas/water ratio, ionic strength, incubation temperature, and speed of shaking as the assay sample. A four point calibration curve was prepared over a concentration range bracketing that of the assay samples. Protein was stored by freezing at –20° C. and assayed using the modified Lowry method, with bovine serum albumin as the standard (Pace, N. R., et al., Analyzing natural Microbial Populations by rRNA sequence. ASM News 51:4–12 (1985)).

Effects of Trace Metals

To assess the effect of trace copper, medium D was prepared with wither stock solution TN2 or TN2-Cu, transferred to 8-oz (250 mL) bottles, sealed, autoclaved, cooled and inoculated with a 1% inoculum of a stationary phase culture of Pseudomonas KC. Cultures were grown to stationary phase, spiked with carbon tetrachloride, and assayed for carbon tetrachloride transformation.

To assess the effects of trace iron, medium D and precipitate-free medium D were prepared using trace metal stock solutions TN2 and TN2-Fe. Cultures were grown 48 or 72 hours, spiked with carbon tetrachloride, and assayed for carbon tetrachloride transformation. To assess iron inhibition, 10 mL of early stationary phase culture (grown for 72 hours in precipitate-free medium D) was transferred to 28 mL serum tubes in an anaerobic glove box, spiked with 0–20 $\mu$M ferric iron (as ferric ammonium sulfate), and equilibrated for 10 minutes. The serum tubes were sealed with Teflon®-lined rubber stoppers, spiked with carbon tetrachloride, shaken throughout the experiment on a shaker table, and monitored by sampling of the gas phase.

Transformation in Groundwater and Soil Systems

The groundwater used in bioaugmentation experiments was Michigan State University tap water. After adjusting the pH of the groundwater to 8.2 with 3N KOH, unsterilized groundwater or filter-sterilized (0.22 $\mu$filter) groundwater was dispensed into a suite of autoclaved 120 mL serum bottles. Some bottles serves as uninoculated controls for abiotic losses. The remainder were inoculated with 1% inoculum of strain KC grown on 1% Nutrient Broth (Difco Co.). Some of the inoculated bottles were autoclaved, while others received additions of acetate (300 mg/L as sodium acetate) and nitrate (200 mg/L as sodium nitrate). The headspace above all samples was replaced with nitrogen, but no effort was made to remove oxygen dissolved in the water. All bottles were sealed with Teflon®-lined rubber stoppers, spiked with 1.5 $\mu$g carbon tetrachloride, placed on a shaker table, and monitored by sampling of the gas phase.

Soil slurry experiments were conducted using Metea type soil from the B horizon at Michigan State University (0.7% organic matter, 31 ppm iron, 4.8 ppm nitrate and 9.9 ppm ammonia). Soil slurries (286 g in 100 mL tap water) adjusted to pH 8.2 with 3N KOH were dispensed into 120 mL serum vials. Some samples were sealed and autoclaved to serve as abiotic controls for sorption and volatilization losses. Controls for the possible transformation of carbon tetrachloride by indigenous microflora were prepared by sealing serum bottles with or without the addition of acetate (300 mg/L as sodium acetate) and nitrate (200 mg/L as sodium nitrate). The remaining bottles received a 1% inoculum of strain KC (grown on precipitate-free medium D) giving an initial cell density of $5 \times 10^2$ cells/mL. Some of the inoculated bottles were amended with acetate (300 mg/L as sodium acetate) and nitrate (200 mg/L as sodium nitrate). The headspace above all samples was replaced with nitrogen, but no effort was made to remove dissolved oxygen. All samples were sealed with Teflon®-lined rubber stoppers, spiked with 1.5 $\mu$g carbon tetrachloride, placed on a shaker table, and monitored by sampling of the gas phase.

RESULTS OF EXPERIMENTS

FIG. 1 and Table 1 show the effect of pH on growth yield of PsKC and on carbon tetrachloride transformation by PsKC in soil. Growth yield increased between pH 7.8 and 9.0. Also, a conmittant significant difference in carbon tetrachloride transformation occurred between 7.3 and 8.2.

TABLE 1 pH dependence of growth yield of PsKC.
Precipitate free Media D was prepared at various
pH and inoculated with 1% 72 hour grown PsKC
culture. Protein was determined after 72 hours
growth by the method of Lowry. All values are
averages of duplicate cultures.
pH dependence or growth yield of Pseudomonas KC

| pH growth media | yield (ug protein/ml) |
| --- | --- |
| 7.4 | 3.3 |
| 7.8 | 6.3 |
| 8.0 | 11.3 |
| 8.2 | 14.0 |
| 8.5 | 14.3 |
| 9.0 | 21.2 |
| 10.0 | 0 |

TABLE 2

Shows the transformation of CT by PsKC
was shown to be first order for cell protein and
first order with respect to substrate
concentration(Sittig, M. Ed., Handbook of Toxic and
Hazardous Chemicals and Carcinogens, 2d Ed., Noyes Pubs.
N.Y. (1985)). Pseudo second order rate
constants were determined for transformation of
CT by cultures grown in various media. All
values represent the averages of three
independent cultures showing standard deviations.
Pseudo- Second Order Rate Coefficients for Co- Metabolism
of Carbon Tetrachloride

| Media | Growth time (hrs) | k' (L/mg protein/day) |
| --- | --- | --- |
| Media D | 48 | 0.893 +/− 0.03 |
|  | 72 | 0.362 +/− 0.08 |
| Precipitate free Media D | 48 | 6.18 +/− 0.48 |
|  | 72 | 2.28 +/− 0.45 |
| Media D-Fe | 48 | 3.93 +/− 1.48 |
|  | 72 | 4.03 +/− 0.79 |
| Precipitate free Media D-Fe | 48 | 9.07 +/− 1.24 |
|  | 72 | 4.41 +/− 0.56 |

Figure 2:
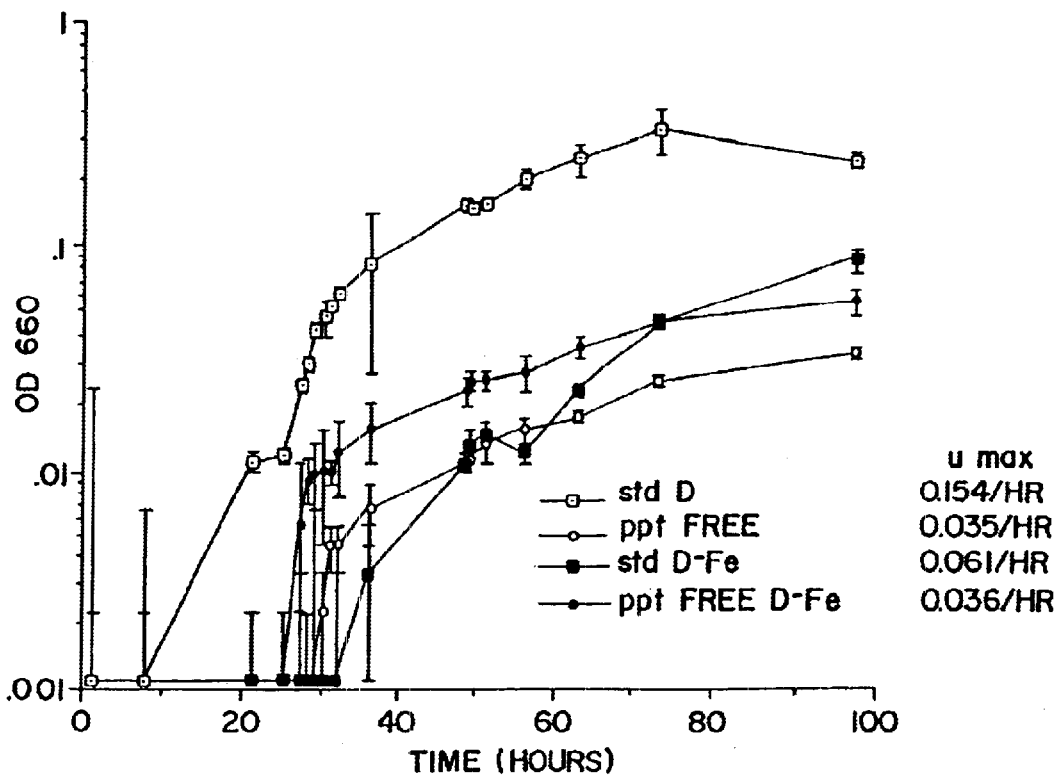
FIG. 2 is a graph showing growth of Pseudomonas KC in medium D with and without modification (iron and/or precipitate free). All values represent averages of triplicate cultures, and error bars indicate the standard deviations.

As shown in Table 2, pseudo-second order rate coefficients for carbon tetrachloride transformation generally decreased as cultures aged from 48 to 72 hours, indicating decay of transformation activity as cells entered the stationary phase. The exception was cultures grown in medium D with TN2-Fe. These cultures continued to grow between 48 and 72 hours, and showed no decrease in the second order rate coefficient over this period. Growth rates for these cultures were higher and less variable than those of cultures grown in precipitate-free media (FIG. 2). These observations suggest that, for this medium, cell growth and production of carbon tetrachloride transformation activity may be controlled by the solubilization of iron in the precipitate.

Transformation in Groundwater and Soil Systems

Figure 3:
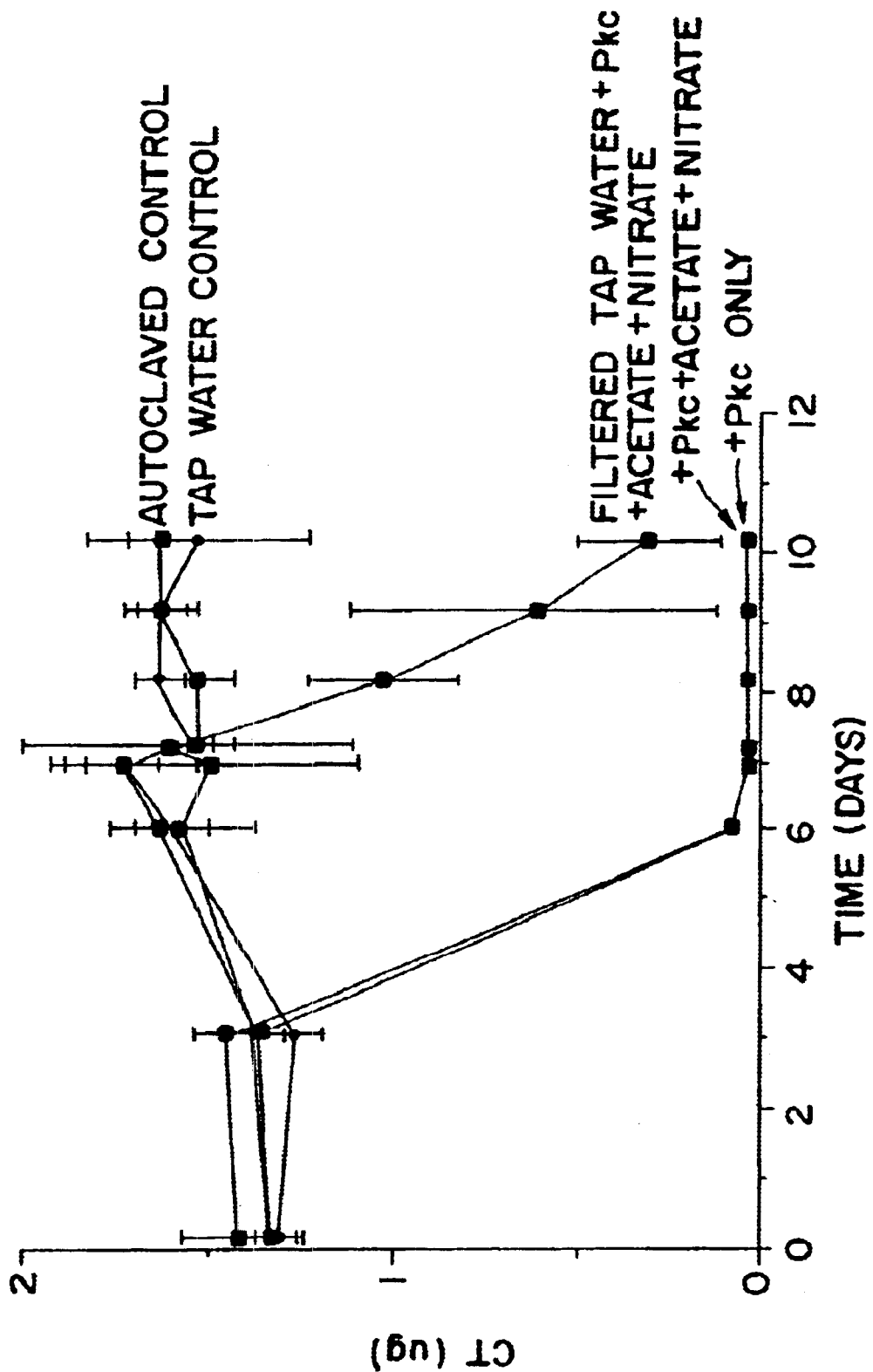
FIG. 3 is a graph showing transformation of CT in alkaline water. Groundwater (MSU tap water containing 0.051 mg Fe/l) was made alkaline by addition of KOH (pH 8.2). 100 ml samples were dispensed into 120 ml serum vials. The headspace was replaced with nitrogen gas and additions made as indicated. +pkc=inoculated with 1% Nutrient Broth (Difco) grown Pseudomonas KC culture. +acetate=300 mg/l sodium acetate, +nitrate=200 mg/l sodium nitrate. Filtered tap water was pre-sterilized using a 0.22 μm filter. All values represent averages of three independent cultures, and the error bars indicate the standard deviations.
Figure 4:
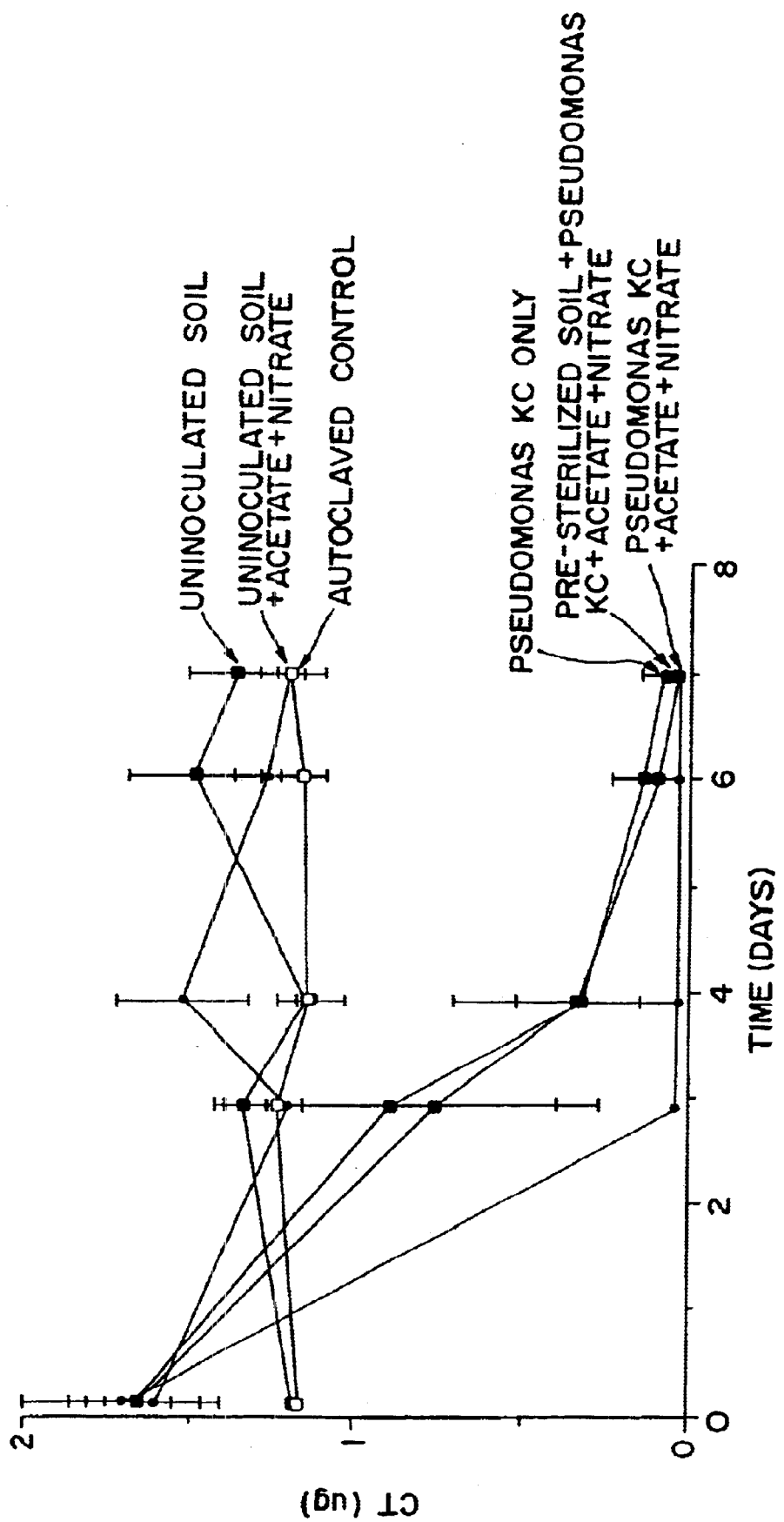
FIG. 4 is a graph transformation of CT in soil. 286 g sandy Michigan soil (Metea type soil, B horizon, MSU campus) per liter tap water was prepared as a slurry and the pH was raised to 8.2 by addition of KOH. Samples (100 ml) were dispensed into 120 ml serum vials. Headspace was replaced with nitrogen and additions made as indicated. +pseudomonas KC=1% inoculum of precipitate free media D grown culture ($5 \times 10^2$ cells/ml initial cell density). +acetate=300 mg/L sodium acetate. +nitrate=200 mg/L sodium nitrate. All values represent averages of three independent cultures, and the error bars indicate the standard deviations.
Figure 5:
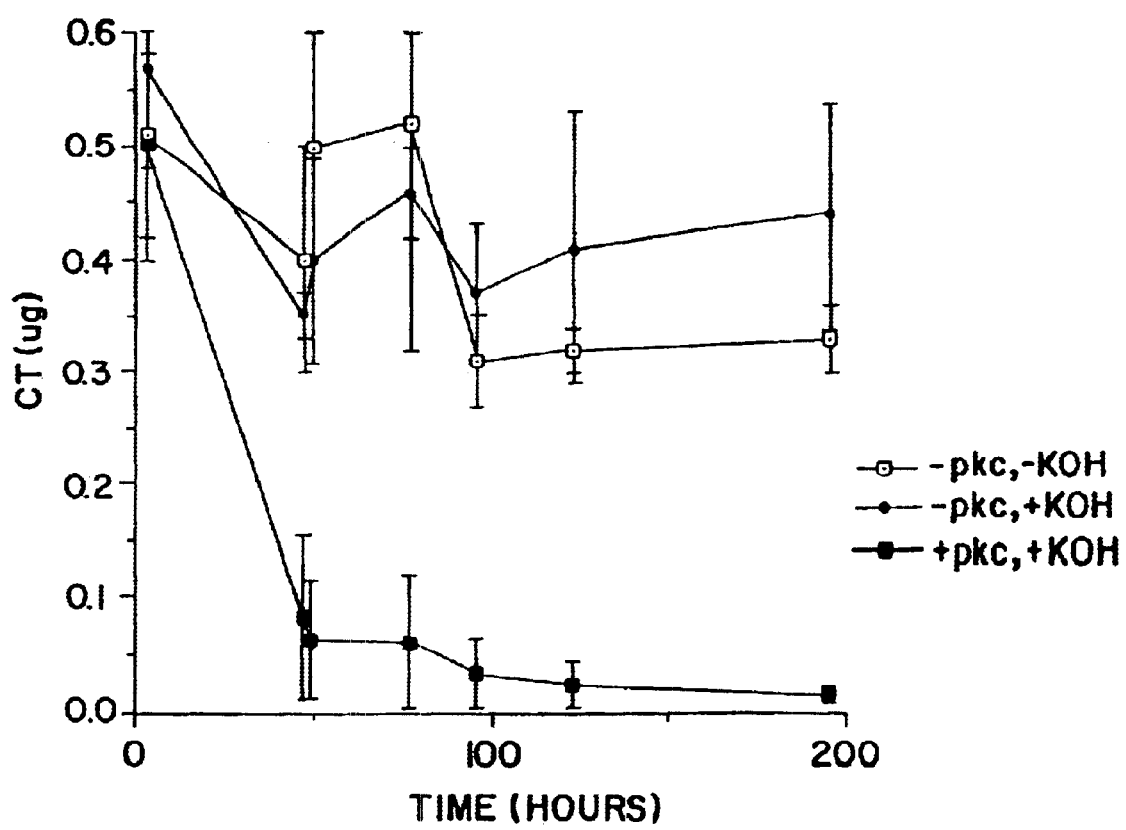
FIG. 5 is a graph showing transformation of CT in groundwater from a CT contaminated aquifer in Schoolcraft, MI. 10 ml samples of groundwater were dispensed in Balch tubes under nitrogen. pH was adjusted to 8.2 as indicated by +KOH, and Pseudomonas KC (1% inoculum, nutrient broth o/n culture) added as indicated by +pkc. Values represent averages of three independent cultures, and the error bars indicate the standard deviations.

As shown in FIGS. 3, 4 and 5, inoculation of groundwater or soil slurries (pH adjusted to 8.2) with Pseudomonas sp. strain KC increased the rate of carbon tetrachloride transformation. Carbon tetrachloride did not disappear in pH-adjusted controls that were not inoculated with strain KC. Addition of strain KC by itself was a sufficient condition for carbon tetrachloride transformation. Acetate and/or nitrate additions were not required.

The above results demonstrate the functionality and utility of the present invention with regard to converting carbon tetrachloride in a remediating situation directly to carbon dioxide and a non-volatile water soluble fraction. The data further demonstrate the criticality of the pH of the medium for the activity of the break-down of the carbon tetrachloride by the PsKC as well as the criticality of the pH vis-à-vis the persistence of the PsKC strain. Thus, it is demonstrated herein that utilizing the present invention in combination with genetic engineering well-known in the art, the present invention can further be utilized to augment growth of genetically altered PsKC and thereby bioaugment various environments for specifically desired activities. Further, the data demonstrates the functionality and utility of the substantially isolated and pure factor from the supernatant of the growing PsKC. Finally, the experimental data demonstrate the functionality and utility of the inventive method and means for enumerating and monitoring PsKC growth in various environments.

The invention has been described in an illustrative manner, and it is to be understood that the terminology which has been used is intended to be in the nature of words of description rather than of limitation.

Obviously many modifications and variations of the present invention are possible in light of the above teachings.

What is claimed is:

1. A method of remediating an environment of soil or water in situ containing diverse microbial populations and contaminated with carbon tetrachloride which comprises:

(a) first adjusting the environment to a pH of 7.8 to 9.2; and (b) then introducing a culture of Pseudomonas strain sp. KC (PsKC) deposited as DSM 7136 and ATCC 55595 into the environment and under anaerobic conditions, in a number and at a temperature sufficient for the PsKC to convert the carbon tetrachloride directly to carbon dioxide and a nonvolatile water soluble fraction, wherein the PsKC converts the carbon tetrachloride at the pH without producing chloroform and wherein the PsKC has been grown in a culture medium to produce the culture and then introduced into the environment containing the diverse microbial populations.

2. The method of claim 1 wherein in step (b) supplements selected from the group consisting of electron donors, electron acceptors, and nutrients are added to the environment with the PsKC under the conditions and in an amount sufficient to promote the growth of the PsKC.

3. The method of claim 1 wherein culture which is introduced into the environment in step (b) contains 1% by volume of the PsKC.

4. The method of claim 1 wherein the PsKC is grown for 24 to 72 hours to produce the culture with the number of the PsKC which is then introduced into the environment in step (b).

5. The method of claim 1 wherein the PsKC is grown without iron in the culture medium which is available to the PsKC to produce the culture and then introduced into the environment in step (b).

* * * * *